United States Patent
Sosebee et al.

[11] Patent Number: 5,987,358
[45] Date of Patent: Nov. 16, 1999

[54] SEMICONDUCTOR DEVICE PACKAGING AND METHOD OF FABRICATION

[75] Inventors: Thomas G. Sosebee, Lake Jackson; Philip H. Chen, Angleton; Dennis Gibson, Lake Jackson; Kenneth R. Ulmer, Brazoria, all of Tex.

[73] Assignee: Intermedics, Inc., Angleton, Tex.

[21] Appl. No.: 09/024,541

[22] Filed: Feb. 17, 1998

[51] Int. Cl.⁶ .................................................. A61N 1/375
[52] U.S. Cl. ................................................. 607/36; 607/5
[58] Field of Search ........................................... 607/36, 5

[56] References Cited

U.S. PATENT DOCUMENTS

| | | |
|---|---|---|
| 4,800,883 | 1/1989 | Winstrom . |
| 4,815,469 | 3/1989 | Cohen et al. . |
| 5,370,669 | 12/1994 | Daglow et al. . |
| 5,620,476 | 4/1997 | Truex et al. . |
| 5,674,260 | 10/1997 | Weinberg . |
| 5,750,926 | 5/1998 | Schulman et al. ............... 174/52.3 |
| 5,814,090 | 9/1998 | Latterell et al. ...................... 607/36 |
| 5,855,995 | 1/1999 | Haq et al. . |

Primary Examiner—William E. Kamm
Assistant Examiner—Carl H. Layno
Attorney, Agent, or Firm—Schwegman, Lundberg, Woessner & Kluth, P.A.

[57] ABSTRACT

A sub-assembly module for surface mounting on an implantable medical device hybrid module is provided. The sub-assembly module includes one or more electronic components mounted on a substrate. Interconnection between the electronic components and the hybrid module is established by bond pads on the upper and lower surfaces of the substrate and thru-substrate conducting plugs connecting respective upper and lower bond pads. The electronic components are encapsulated in a layer of insulating material. The electronic components may be chip-and-wire mounted to the sub-assembly module and the sub-assembly module may, in turn, be surface mounted to the hybrid module, permitting the integration of chip-and-wire and surface mount processing for a given hybrid module.

7 Claims, 4 Drawing Sheets

SEMICONDUCTOR DEVICE PACKAGING AND METHOD OF FABRICATION

BACKGROUND OF THE INVENTION

1. Field of the Invention

This invention relates generally to implantable cardiac stimulators, and more particularly to circuit modules encased within cardiac stimulators.

2. Description of the Related Art

The advent of implantable cardiac stimulation systems, such as pacemakers and defibrillators, has brought welcome relief to many patients suffering from various forms of cardiac arrhythmia. Conventional cardiac stimulator systems typically consist of a cardiac stimulator and one or more elongated leads. The cardiac stimulator may be a pacemaker, a defibrillator, a sensing instrument, or some combination thereof. The circuitry, batteries, and other components of the cardiac stimulator are ordinarily encased within a metallic housing commonly referred to as a "can." Most of the electronic components for the cardiac stimulator are mounted on a small circuit board commonly known as a multi-chip or hybrid module.

The proximal ends of the leads of the cardiac stimulator system are connected physically and electrically to the cardiac stimulator via a structure commonly known as a header. The distal end of the lead is implanted near the site requiring electrical stimulation or sensing. The leads function to carry electrical signals from the cardiac stimulator to the targeted tissue and signals from the targeted tissue back to the cardiac stimulator.

For most implantable cardiac stimulators, implantation requires an incision in the right or left pectoral region above the areola and formation of a pocket in the subcutaneous tissue by blunt dissection. The leads are then passed into the body to the sites requiring electrical stimulation, usually with the aid of a stylet. The proximal ends of the leads are then connected to the header of the cardiac stimulator and the cardiac stimulator is inserted through the incision and placed in the pocket. The incision is then closed by conventional suturing. The post-operative appearance of the implant area will depend to a large degree on the size of the cardiac stimulator.

A conventional multi-chip module consists of a number of electronic devices disposed on one or both sides of a flat insulating substrate. Depending upon the type of cardiac stimulator, the devices may be discrete devices, such as resistors and capacitors, or more highly integrated devices, such as power transistors, microprocessors, telemetry circuits, or induction coils for rechargeable storage devices. Depending on the manufacturer, the components may be packaged, unpackaged, or a combination of the two.

Surface mounting and chip-and-wire represent two common techniques for mounting both packaged and unpackaged components on a multi-chip module. For packaged parts, surface mounting involves coupling the package to the multi-chip module by soldering the pins of the package to metal traces on the multi-chip module. The package may be further secured by an adhesive. The package pins provide connectivity with the enclosed component via bonding wires protected by the package. In a variant of surface mounting known as flip-chip, an unpackaged part fabricated on a die, such as an application specific integrated circuit ("ASIC") or microprocessor, is mounted directly on the multi-chip module. The bond pads on the die are typically bump connected to metallization on the multi-chip module. Flip chip mounting technology has the advantage of potentially high packing density. However, for components that are traditionally supplied in packaged form, such as diodes and resistors, the footprints of the packages are relatively large and represent a limit on the achievable packing density for the multi-chip module.

In chip-and-wire mounting, unpackaged components are secured to the multi-chip module by an adhesive and connectivity with the multi-chip module is established by bonding wires connected between the bond pads of the component and metallization on the multi-chip module. Chip-and-wire mounting can achieve higher packing density than is possible in surface mounting for those types of components supplied in packages with large footprints. However, conventional chip-and-wire processing is generally incompatible with surface mount processing. The problem stems from the fact that the solder and solder flux used to mount a surface mount package may short or damage the tiny bonding wires connecting the bonding pads of a bare die to the multi-chip module substrate. Aside from incompatibility with surface mount processing, conventional chip-and-wire mounted components must be separately tested. Such component-by-component electrical testing adds to cost of the overall manufacturing process.

One method currently used in attempt to alleviate the incompatibility problem involves mounting bare die on one side of the multi-chip module substrate using chip-and-wire processing, and surface mounting other components on the opposite side of the multi-chip module substrate. A drawback associated with this method is that complex metallization must be fabricated on both sides of the multi-chip module substrate and the overall thickness of the multi-chip module is increased.

The present invention is directed to overcoming or reducing one or more of the foregoing disadvantages.

SUMMARY OF THE INVENTION

In accordance with one aspect of the present invention, a sub-assembly module for surface mounting on an implantable medical device hybrid module is provided. The sub-assembly module includes a substrate, a first conductor coupled to the substrate, and a second conductor coupled to the substrate. An electronic component is coupled to the substrate and is connected between the first conductor and the second conductor. A layer of insulating material is coupled to the substrate and encapsulates the electronic component and the first and second conductors.

In accordance with another aspect of the present invention, a method of fabricating a sub-assembly module for surface mounting on an implantable medical device hybrid module is provided. The method includes the steps of providing a substrate, coupling a first conductor to the substrate, and coupling a second conductor to the substrate. An electronic component is coupled to the substrate and connected between the first and second conductors. A layer of insulating material is applied on the electronic component and the first and second conductors.

In accordance with still another aspect of the present invention, a sub-assembly module for surface mounting on an implantable medical device hybrid module is provided. The sub-assembly module includes a substrate that has an upper side and a lower side. A first conductor is coupled to the substrate and a second conductor is coupled to the substrate. Each of the first and second conductors has a first bond pad coupled to the upper side, a second bond coupled to the lower side, and a conducting plug connecting the first and second bond pads. An electronic component is coupled to the substrate and is connected between the first conductor and the second conductor. A layer of insulating material is coupled to the substrate and encapsulates the electronic component and the first bond pads of the first and second conductors.

In accordance with another aspect of the present invention, a cardiac stimulator is provided. The cardiac stimulator includes a can, a hybrid module disposed in the can, and a sub-assembly module coupled to the hybrid module. The sub-assembly module has a substrate, a first conductor coupled to the substrate, a second conductor coupled to the substrate, an electronic component coupled to the substrate and connected between the first conductor and the second conductor, and a layer of insulating material coupled to the substrate and encapsulating the electronic component and the first and second conductors.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
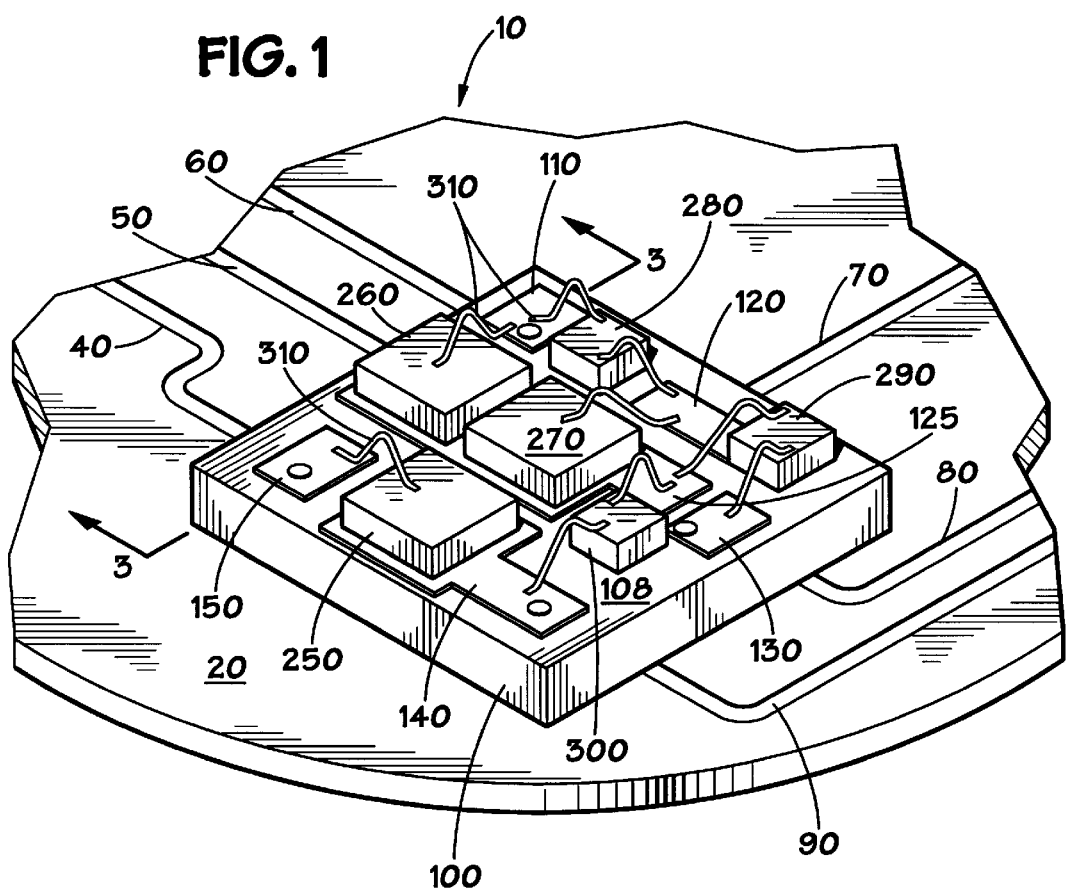
FIG. 1 is a pictorial view of an exemplary embodiment of a sub-assembly module surface mounted on a hybrid module in a cardiac stimulator in accordance with the present invention.
Figure 2:
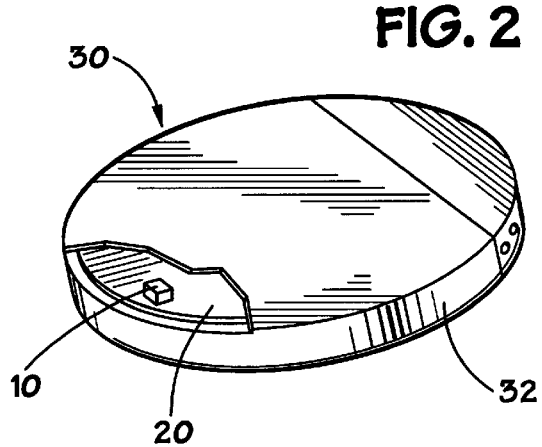
FIG. 2 is a pictorial view of the cardiac stimulator of FIG. 1 in accordance with the present invention.

In the drawings described below, reference numerals are generally repeated where identical elements appear in more than one figure. Turning now to the drawings, and in particular to FIGS. 1 and 2, there is shown therein an exemplary embodiment of a sub-assembly module 10 in accordance with the present invention. FIG. 1 is a highly magnified pictorial view of the sub-assembly module 10 surface mounted on a hybrid module 20 of a cardiac stimulator 30 shown in FIG. 2. The sub-assembly module 10 includes a protective encapsulation layer to be described below. However, for clarity of illustration, the encapsulation layer is not shown in FIG. 1. FIG. 2 is a pictorial view of the cardiac stimulator 30 and is partially cut away to reveal the portion of the hybrid module 20 depicted in FIG. 1 and the sub-assembly module 10 mounted thereon. The hybrid module 20 holds various power, control, and other circuitry for the cardiac stimulator 30. The cardiac stimulator 30 may be a cardiac stimulator, such as a pacemaker, a cardioverter/ defibrillator, a sensing instrument, or some combination of these instruments. Although a cardiac stimulator is illustrated, it is contemplated that the invention may be applied to other types of implantable devices, such as infusion pumps.

The hybrid substrate 20 is composed of an insulating ceramic material, such as aluminum oxide or similar materials, or plastic materials, such as polycarbonate plastic or like plastic materials. The hybrid 20 is provided with a number of metallization traces for conveying electrical signals to and from the sub-assembly module 10 and/or other components of the cardiac stimulator 30. Six of the traces connected to the sub-assembly module 10 are illustrated at 40, 50, 60, 70, 80, and 90.

The sub-assembly module 10 is designed to integrate one or more electronic components into a structure that is surface mountable on the hybrid substrate 20. As noted above, various technologies may be employed to mount electronic components to the hybrid module 20, including chip-and-wire, surface mounting, and flip-chip. Flip-chip solder mounting offers the advantage of potentially tight packing density for mounting many types of electronic components to a hybrid module. However, less than desirable packing density may be achieved for some discrete components frequently used in cardiac stimulators, such as diodes and resistors. When supplied in surface mountable packages, such discrete components frequently have relatively large footprints that may hamper packing density. Chip-and-wire mounting techniques can yield higher packing density for such discrete components. However, as noted above, conventional chip-and-wire mounting processes are generally not compatible with conventional surface mounting processes.

Figure 3:
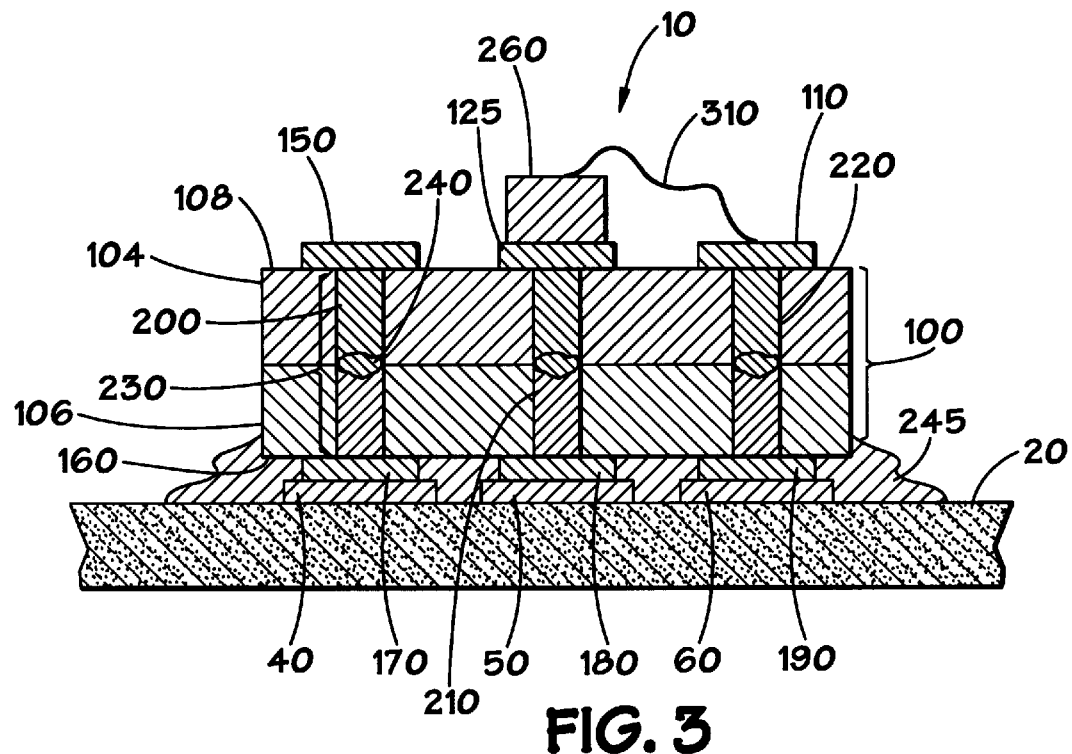
FIG. 3 is a cross-sectional view of FIG. 1 taken at section 3—3 in accordance with the present invention.

The sub-assembly module 10 integrates surface mounting technology with chip-and-wire technology to take advantage of the inherent advantages of both technologies. The sub-assembly module 10 can hold a number of chip-and-wire mounted components in a structure that is surface mountable to the hybrid module 20. In this regard, the sub-assembly module 10 includes a substrate 100 that is surface mounted to the hybrid module 20. Referring now also to FIG. 3, which is a cross-sectional view of FIG. 1 taken at section 3—3, the substrate 100 may be composed of an insulating ceramic material, such as aluminum oxide or similar materials, or plastic materials, such as polycarbonate plastic or like plastic materials. The substrate 100 is advantageously composed of Green Tape® uncured substrate supplied by the DuPont Corporation. In the illustrated embodiment, the substrate 100 consists of an upper sheet 104 and a lower sheet 106 compressed into a single structure under high pressure and cured in a low temperature fire process at approximately 850 to 860° C. for approximately 10 to 20 minutes.

Still referring to FIGS. 1 and 3, the substrate 100 has an upper surface 108 provided with metallization bond pads 110, 120, 125, 130, 140, and 150. Each of the bond pads 110, 120, 125, 130, 140, and 150 is connected to a corresponding bond pad disposed on the lower side 160 of the substrate 100. Three of the bond pads on the lower side 160 are illustrated in FIG. 3 and designated 170, 180, and 190. The other three bond pads on the lower side 160 are not visible. The bond pads 110, 120, 125, 130, 140, and 150 are advantageously composed of gold or other suitable solderable conducting materials and are fabricated on the substrate 100 using well known metallization stencil and printing techniques. The bond pads 110, 120, 125, 130, 140, and 150 on the upper surface 108 are patterned and printed to accommodate the various electronic components mounted on the substrate 100. Similarly, the various bond pads on the lower surface 160 are patterned and printed to align with and contact particular traces on the hybrid module 20.

Interconnection between two corresponding bond pads, such as the bond pads 150 and 170, is established by a contact plug 200 disposed in the substrate 100. Identical contact plugs 210 and 220 are provided to interconnect the bond pads 125 and 180 and the bond pads 110 and 190. The following description of the plug 200 is illustrative of the other plugs in the sub-assembly module 10. Prior to application of the bond pads 150 and 170, a via 230 is formed in the upper and lower halves 104 and 106 of the substrate 100. The vias 230 may be mechanically punched or laser drilled and are advantageously mechanically punched. The via in each half 104 and 106 is filled with a suitable conducting material, such as gold, silver palladium alloy, or like conducting material. After the plug 200 is deposited, the bond pads 150 and 170 are printed and the two halves 104 and 106 of the substrate 100 are fused together under high pressure to form the substrate 100 as shown. The plug 200 will consist of the conducting material deposited in the vias in the upper and lower halves 104 and 106 and compressed together at 240.

As shown in FIG. 3, the substrate 100 is surface mounted to the hybrid module 20 so that connections are established between the bond pads 170, 180, and 190 on the lower side 160 of the substrate 100 and corresponding traces 40, 50, and 60 on the hybrid module 20. Similar pathways are established between the pads 120, 130, and 140 and the traces 70, 80, and 90. The substrate 100 may be coupled to the hybrid module 20 by a conducting epoxy, such as Able Bond 85-1 or like epoxies, by non-conducting epoxy, such as Able Bond 84-3 or like epoxies, or by soldering. The epoxy material may be applied to the hybrid module 20 by screen printing or by dispensing via a controlled dispenser. In lieu of adhesives, a number of well known bump connecting techniques may be used, such as non-melting high temperature bump soldering, completely melting bump soldering, partially melting bump soldering (copper core), as well as other techniques, such as application of a Z-axis conductive polymer material, or similar techniques.

If the substrate 100 is connected to the hybrid 20 by bump soldering, the area between the substrate 100 and the hybrid module 20 may be filled with a polymeric underfill material that not only provides a cushion between the substrate 100 and the hybrid substrate 20, but also provides protection against thermal cracking that may result from thermal stresses created by the dissimilar thermal conductivities of the sub-assembly module 10 and the hybrid substrate 20. The layer 245 in FIG. 3 is depicted to represent either the aforementioned epoxy adhesive where epoxy is used to secure the substrate 100, or the aforementioned underfill material in the event bump soldering is employed.

Figure 4:
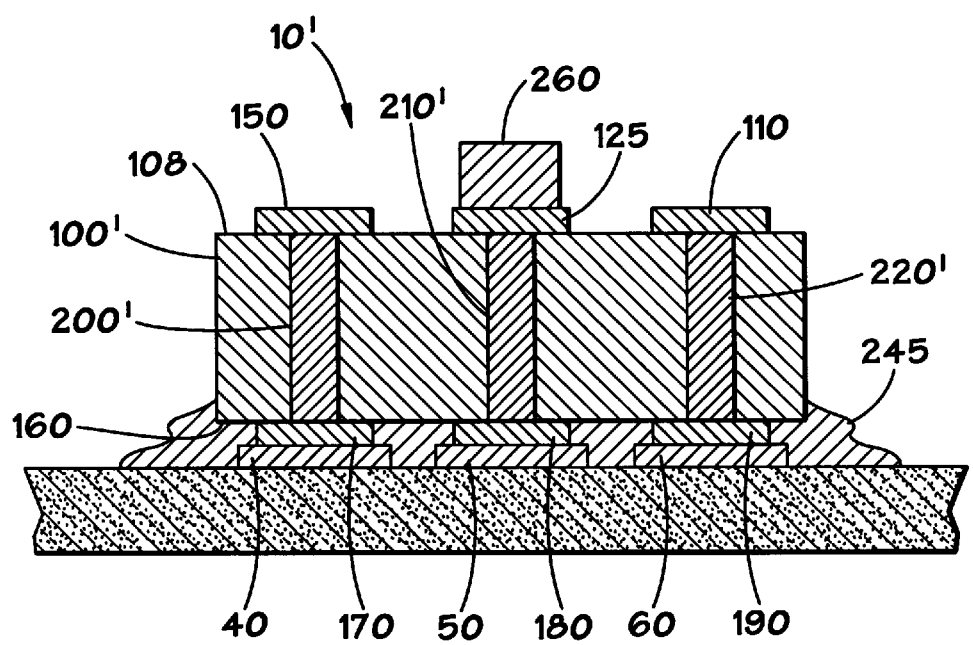
FIG. 4 is a cross-sectional view like FIG. 3 of an alternate embodiment of the sub-assembly module in accordance with the present invention.

In an alternate embodiment of the sub-assembly module 10' depicted in FIG. 4, the substrate, now designated 100', is fabricated as a unitary structure. In this embodiment, the vias 230 are advantageously laser drilled. The plugs, now designated 200', 210', and 220', are deposited and fired at approximately 850 to 860° C. for approximately 10 to 20 minutes. The bond pads 110, 125, 150, 170, 180 and 190 are patterned and printed as generally described above. The substrate 100' may be composed of alumina ceramic of various compositions, and is advantageously 96% alumina substrate available from Coors, Inc. or Kyocera.

Referring again to FIGS. 1 and 3, various electronic components are chip-and-wire mounted on the substrate 100. In the illustrated embodiment, the electronic components include diodes 250, 260, and 270, and resistors 280, 290, and 300. However, the components may be integrated circuits such as ASICs, microprocessors, or other types of integrated circuits. The person of ordinary skill in the art will appreciate that the type, number, and arrangement of the particular electronic components is largely a matter of design discretion. The diodes 250, 260, and 270 and the resistors 280, 290, and 300 are secured to the substrate 100 by a conducting epoxy, such as Able Bond 85-1 or like epoxies, or a non-conducting epoxy such as Able Bond 84-3 or like epoxies. The epoxy material may be applied to the substrate 100 by screen printing or by dispensing via a controlled dispenser. Following application to the substrate 100, the epoxy material is cured at approximately 150° C. for approximately 1 hour.

Figure 5:
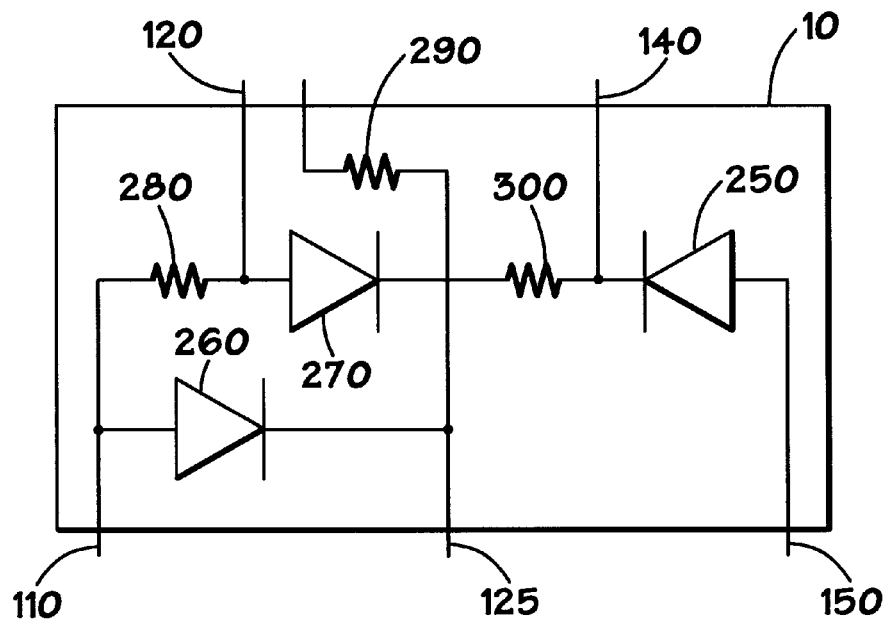
FIG. 5 is a schematic view of the circuitry of the sub-assembly module of FIG. 1 in accordance with the present invention.

The interconnection of the various electronic components on the sub-assembly module 10 may be understood by referring now also to FIG. 5, which is a schematic of the sub-assembly module 10. The inputs to the diode 260 and the resistor 200 are commonly connected to the bond pad 110 by conductors or bonding wires 310. Note that only the bonding wires 310 are individually labeled. The other bonding wires depicted for the various electronic components are virtually identical and are not separately labeled for clarity of illustration. One terminal of the resistor 200 and the input of the diode 270 are commonly connected to the bond pad 120. One terminal of each of the resistors 290 and 300 and the outputs of the diodes 270 and 250 are commonly connected to the bond pad 125. The input to the diode 250 is connected to the bond pad 150 and the output of the diode 250 and the other terminal of the resistor 300 are commonly connected to the bond pad 140. The bonding wires 310 are advantageously composed of gold or like conducting materials and may be applied by well known thermal or ultrasonic techniques for installing bonding wires. Prior to installation of the bonding wires 310, the substrate 100 is advantageously plasma cleaned in an inert ambient, such as argon, to remove any excess epoxy or other contaminants from the bond pads 110, 120, 125, 130, 140, and 150.

The combination of a given bond pad, such as 125, and an associated plug 210 and a bond pad 180 provides a first conductor. Similarly, the combination of another given bond pad, such as 140, and an associated plug 220 and a bond pad 190 provides a second conductor. A circuit between the component 260 and the hybrid 20 is established by connecting the component 260 between the two conductors. Other arrangements may be used to establish the pathway, such as trace and bonding wire, or other arrangements.

Figure 6:
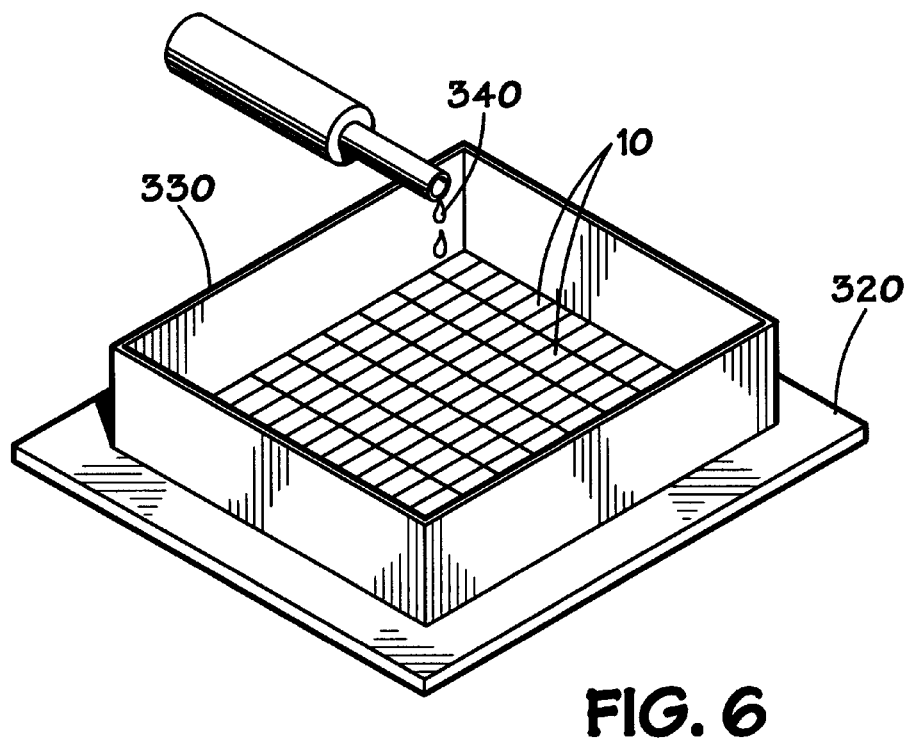
FIG. 6 is a pictorial view of a plurality of sub-assembly modules in a wafer during application of an encapsulation layer in accordance with the present invention.

As noted above, the sub-assembly module 10 is depicted in FIGS. 1, 3 and 4 with a protective encapsulating layer removed to reveal the underlying structures. The structure and application of the encapsulating layer will now be described. FIG. 6 is a pictorial view of a wafer 320 of the material used to form the substrate 100 described above. A plurality of identical sub-assembly modules 10, represented by the rectangles, are advantageously produced en masse on the wafer 320 by applying the techniques, described above in the context of a single sub-assembly module 10, to the wafer 320. A form 330 is temporarily applied to the wafer 320 to contain the encapsulating material during subsequent hardening. The form 330 should be slightly higher than the desired thickness of the encapsulating layer, and may be glued to the wafer 320. The form 330 is advantageously composed of a ceramic material, such as $Al_2O_3$, or like materials. The encapsulating material 340 is poured into the form 330 until all of the bonding wires of the plurality of sub-assembly modules 10 are covered. The material 340 is thermally cured to form a self-planarizing, hardened protective coating over the sub-assembly modules 10.

The encapsulating material 340 is advantageously an electrically insulating material that may be readily poured over the wafer 320 and cured to form a relatively smooth protective coating. The particular curing protocol will depend on the type of material used. In the illustrated embodiment, the encapsulating material 340 is Hysol FP4650 and is cured at approximately 125° C. for approximately 1 hour, then at approximately 165° C. for approximately 2 hours.

Figure 7:
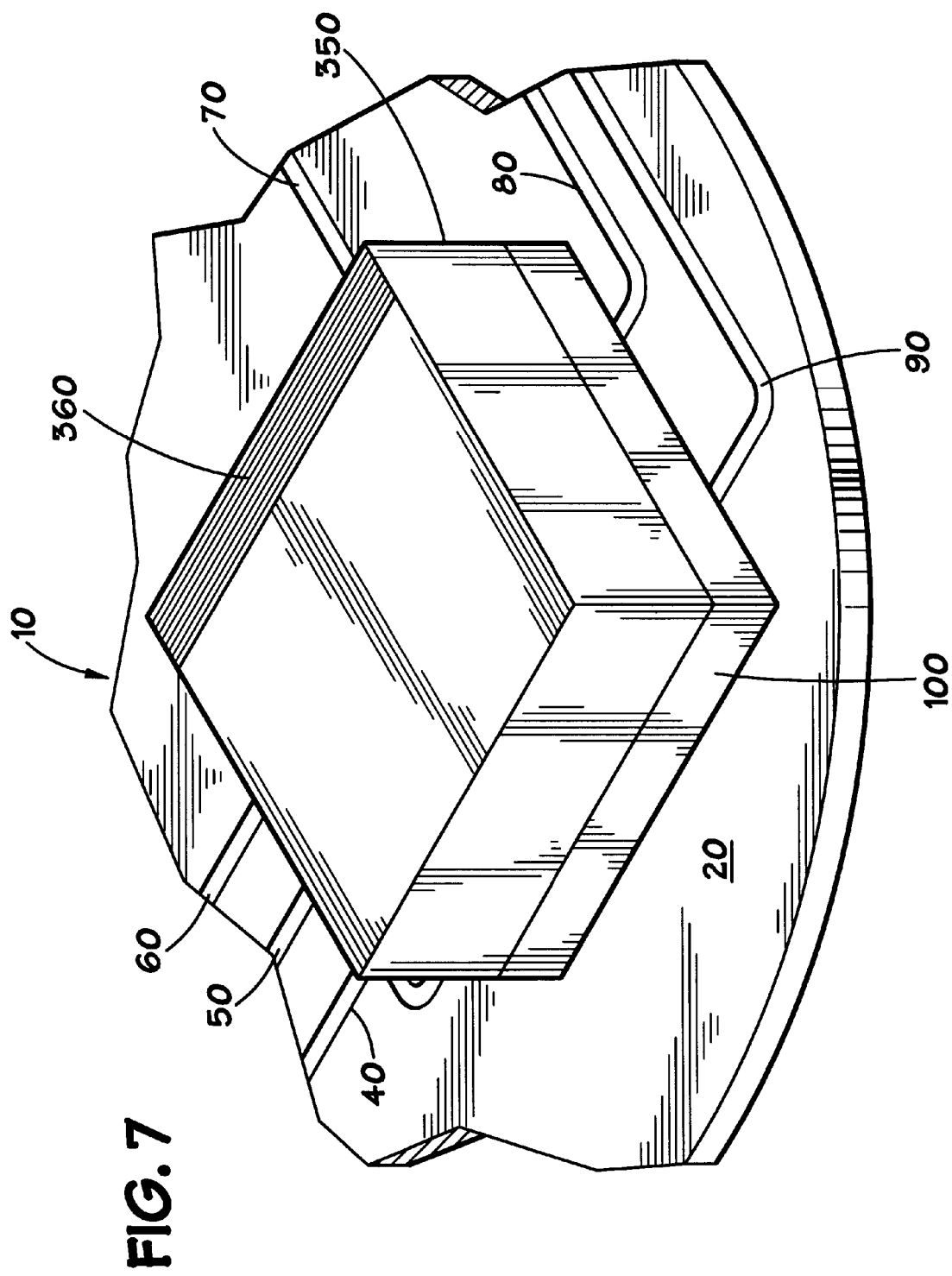
FIG. 7 is a pictorial view like FIG. 1 showing the sub-assembly module with the encapsulation layer in place in accordance with the present invention.

After the material 340 is cured, the form 330 may be removed and the individual sub-assembly modules 10 diced to yield completed sub-assembly modules 10, one of which is depicted in FIG. 7. The encapsulating layer 350 protects the delicate bonding wires and the various components of the sub-assembly module 10 from structural damage that might otherwise occur when the sub-assembly module 10 is mounted on the hybrid module 20. The encapsulating layer 350 also protects the components and the bonding wires from solder flux or other contaminants presented during subsequent processing of the hybrid module 20.

Referring to FIG. 7, the top of the encapsulation layer 350 may be provided with an orientation mark 360 to identify the relative orientations of the various components and conductors of the sub-assembly module 10. The orientation mark 360 say be provided in a variety of forms, such as a painted strip shown in FIG. 7, an imprinted marking, or some other type of marking.

The complete sub-assembly module 10 achieves the advantageous packing density of chip-and-wire mounted discrete components in a surface-mount compatible structure. Manufacturing and testing time savings may be realized since the sub-assembly module 10 may be electrically tested as a unit, providing a known-good-module testing capability. Moreover, the relatively planar surface of the encapsulating layer 350 is ideally suited for automated pick-and-place equipment.

The skilled artisan will appreciate that the sub-assembly module 10 may be used to integrate devices other than discrete components. For example, one of the components, such as the diode 170 shown in FIG. 1, may be replaced with an integrated circuit, such as a microprocessor or an ASIC.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method of fabricating a sub-assembly module for surface mounting on an implantable medical device hybrid module, comprising the steps of:

providing a substrate;

coupling a first conductor to the substrate;

coupling a second conductor to the substrate;

coupling an electronic component to the substrate and connecting the electronic component between the first and second conductors; and applying a layer of insulating material on the electronic component and the first and second conductors.

2. The method of claim 1, wherein the step of coupling the electronic component comprises applying a layer of conductive epoxy to the substrate and placing the electronic component on the conductive epoxy.

3. The method of claim 1, wherein the step of applying the layer of insulating material comprises encircling the substrate with a form, pouring the insulating material into the form until the electronic component and the first and second conductors are covered, and hardening the material by heating.

4. The method of claim 1, wherein the step of connecting the electronic component to the second conductor comprises coupling a bonding wire between the electronic component and the second conductor.

5. A cardiac stimulator comprising:

a can;

a hybrid module disposed in the can; and a sub-assembly module coupled to the hybrid module, the sub-assembly module having a substrate, a first conductor coupled to the substrate, a second conductor coupled to the substrate, an electronic component coupled to the substrate and being connected between the first conductor and the second conductor, a bonding wire connecting the electronic component to the second conductor, and a layer of insulating material coupled to the substrate and encapsulating the electronic component and the first and second conductors.

6. The sub-assembly module of claim 1, wherein the electronic component comprises an integrated circuit.

7. The sub-assembly module of claim 1, wherein the electronic component comprises a diode.

\* \* \* \* \*

UNITED STATES PATENT AND TRADEMARK OFFICE
CERTIFICATE OF CORRECTION

PATENT NO.: 5,987,358

DATED: November 16, 1999

INVENTOR(S): Thomas G. Sosebee, Phillip H. Chen, Dennis Gibson, Kenneth R. Ulmer It is certified that error appears in the above-identified patent and that said Letters Patent is hereby corrected as shown below:

In column 8, line 45, delete "sub-assembly module of claim 1" and insert --cardiac stimulator of claim 5--.

In column 8, 47, delete "sub-assembly module of claim 1" and insert --cardiac stimulator of claim 5--.

Signed and Sealed this

Thirteenth Day of February, 2001

*Attest:*

NICHOLAS P. GODICI

*Attesting Officer*   Acting Director of the United States Patent and Trademark Office

UNITED STATES PATENT AND TRADEMARK OFFICE
CERTIFICATE OF CORRECTION

PATENT NO.: 5,987,358
DATED: Nov. 16, 1999
INVENTOR(S): Sosebee et al.

It is certified that errors appear in the above-identified patent and that said Patent is hereby corrected as shown below:

In field [56] under References Cited, add the following:

| -- 5,220,491 | U.S. | 6/1993 | Sugano et al. | 607/36 |
| 3442131 | DE | 5/1986 | Möller et al. | H01L 21/56 |
| 92/15368 | PCT | 9/1992 | Carpentier et al. | A61N 1/375 |

"MCM-L Offers Easiest Path to Higher Performance", Electronic Packaging and Production, Vol. 33, No. 12, pp. 48-51, (Dec. 1993) --

Signed and Sealed this

Fifteenth Day of May, 2001

Attest:

NICHOLAS P. GODICI

Attesting Officer

Acting Director of the United States Patent and Trademark Office